United States Patent

LaBarbera

[11] Patent Number: 5,991,651
[45] Date of Patent: Nov. 23, 1999

[54] COMPRESSION/TRACTION METHOD FOR USE WITH IMAGING MACHINES

[76] Inventor: Joseph A. LaBarbera, 26 Blue Heron Dr., Barneveld, N.Y. 13304

[21] Appl. No.: 08/910,276

[22] Filed: Aug. 13, 1997

[51] Int. Cl.⁶ .................................................. A61B 5/055
[52] U.S. Cl. .................................. 600/415; 5/601; 5/622; 5/624; 602/33; 602/36
[58] Field of Search .................................... 600/407, 415; 606/130, 241, 243; 602/32, 33, 35, 36, 40; 5/601, 621, 622, 624

[56] References Cited

U.S. PATENT DOCUMENTS

| | | |
|---|---|---|
| 4,674,483 | 6/1987 | Frederick . |
| 4,854,305 | 8/1989 | Bremer . |
| 4,890,604 | 1/1990 | Nelson . |
| 5,154,186 | 10/1992 | Laurin et al. . |
| 5,217,488 | 6/1993 | Wu . |
| 5,342,290 | 8/1994 | Schuellein . |
| 5,427,116 | 6/1995 | Noone . |
| 5,451,232 | 9/1995 | Rhinehart et al. . |
| 5,476,095 | 12/1995 | Schnall et al. . |
| 5,549,849 | 8/1996 | Kuc et al. . |
| 5,602,809 | 2/1997 | Shikano . |
| 5,662,597 | 9/1997 | Chitwood . |
| 5,680,861 | 10/1997 | Rohling . |
| 5,724,970 | 3/1998 | Votruba et al. ................ 600/415 |
| 5,730,706 | 3/1998 | Garnies . |
| 5,743,264 | 4/1998 | Bonutti ........................... 600/415 |
| 5,807,255 | 9/1998 | Yokota et al. .................. 600/415 |
| 5,810,006 | 9/1998 | Votruba et al. ................ 600/415 |
| 5,836,878 | 11/1998 | Mock et al. ..................... 600/415 |
| 5,899,859 | 5/1999 | Votruba et al. ................ 600/415 |

*Primary Examiner*—Marvin M. Lateef
*Assistant Examiner*—Shawna J. Shaw
*Attorney, Agent, or Firm*—Ralph J. Mancini

[57] ABSTRACT

Compression/traction device for use with internal imaging devices including a stabilizing member for engaging a portion of the thorax of a patient's body and a force generating device to apply a force to the patient's body remote from the thorax. A load simulation table for imaging devices such as X-ray, CAT scan, MRI or tomography instruments is also disclosed, which includes a thorax engaging member and a force generating device to apply a force to the patient's body remote from the thorax portion. A method for simulating a load on a patient's body during imaging procedures is also disclosed and includes the steps of positioning a patient on a flat surface to subject the patient to an imaging procedure, engaging a portion of the thorax of the patient's body, applying a force to a portion of the patient's body at a location remote from the thorax and performing an imaging procedure while applying the force to the patient.

5 Claims, 8 Drawing Sheets

COMPRESSION/TRACTION METHOD FOR USE WITH IMAGING MACHINES

BACKGROUND OF THE INVENTION

1. Technical Field

The present disclosure relates to a device for use with internal imaging machines such as X-ray machines, ultrasound MRI machines, CAT scans and tomography machines, and in particular relates to a compression/traction device for simulating a positive or negative load on a person's body, in particular the person's spine.

2. Discussion of the Prior Art

In recent years, diagnostic instrumentation for creating images of tissue, organs, and bone structure beneath the surface of the skin has been vastly improved, providing detailed and very precise images to enable doctors to determine the cause of internal problems. Accurate diagnosis will of course lead to better care for the patient and in most cases quicker recovery.

Traditional X-ray machines have been supplemented by more complex, and consequently more expensive, diagnostic procedures involving instrumentation such as tomography, which is the recordation of internal body images at a predetermined plane by means of a tomograph. A tomograph is an apparatus for moving an X-ray source in one direction as the film is moved in the opposite direction, thus showing in detail a predetermined plane of tissue. The most well known tomographic procedure is the computerized axial tomography device, typically known as a CAT scan. The CAT scan measures the X-ray beam using a scintillation counter, and the electronic impulses are recorded on a magnetic disc and processed by a mini computer for reconstruction display of the body in cross-section on a cathode ray tube, or television screen. Other popular and frequently used diagnostic imaging machines include nuclear magnetic resonance imaging machines, commonly known as an MRI machine. During an MRI procedure, the body is placed in a spatially varying magnetic field and is subjected to a pulse of radiofrequency radiation, and the resulting nuclear magnetic resonance spectra are combined to give cross-sectional images. Both the CAT scan and MRI techniques provide a very accurate and detailed image of internal body parts to enable the physician to accurately access internal damage to the patient.

However, a problem associated with any internal imaging device, whether it is the traditional X-ray, CAT scan or MRI procedure, is that many times injuries that are apparent to the patient, i.e., cause pain, loss of function, etc., may not be apparent during some imaging procedures since typically the patient is immobilized by placing the patient on a table and his movement is restricted. While providing for an accurate image, many times the injury is "masked" since the person's body weight has been removed from the affected area thus decompressing the joint, disc, cartridge, etc. This is typical with injuries to the spine and to soft tissue in joints, such as the knee, elbow or shoulder. Once the weight ("load") has been removed, many times the severity of the injury may not show up on the image, and in some cases the pain to the patient disappears during the procedure because the causative factor has been reduced enough to decrease irritation and pain production.

In some instances, particularly with soft tissue injuries to joints such as the knee, it may be beneficial to remove the load completely and traction the joint to provide for better imaging, particularly when there is swelling involved or if there is a need to use contrast medium for enhancement. Imaging machines currently available do not provide for either compression (placing a load on the affected area) or traction to enhance the internal image.

Therefore, a need exists for a device which enhances internal imaging utilizing such procedures as CAT scans, MRIs and traditional X-ray devices. The need further exists for a device which will simulate a load on a patient's body when the person is immobilized and laying prone or supine on a table during the imaging procedure. A further need exists for a device which may provide for traction to relieve pressure on the body during the imaging procedure.

SUMMARY OF THE INVENTION

The present disclosure includes a device for use with internal imaging machines which allows the physician to place a load on the patient's body to simulate the patient's body weight or produce a positive force on the internal bone structure, organs, tissue or joints which are being subjected to the internal imaging. The present disclosure also includes a device for placing a portion of the patient's body in traction to remove all loads or produce a negative force on the patient's body during the imaging procedure.

There is disclosed a device for use with an imaging machine to provide compression or traction to the patient's body which includes a stabilizing member for engaging the thorax portion of a patient's body and a means for applying a force to a portion of the patient's body remote from the thorax. The present device may take the form of an attachment to an imaging machine's table, or it may comprise the table itself in which a portion of the table engages a thorax portion of the patient's body while also including a means for applying a force to the patient's body remote from the thorax. The present device may also take the form of a vest or the like which may be worn by the patient.

Generally, the thorax engaging portion comprises a stabilizing member which may include a pair of post members for engaging the upper thorax of the patient's body, either above the shoulders to be applied against the shoulders or under the axilla, or armpits, of the patient's body. A force applying mechanism, typically spring loaded, will then be provided to engage a portion of the patient's body remote from the thorax, either at the feet when used for compression or traction of a lower portion of the patient's body, or for engaging a portion of the head when compressing or tractioning a cervical portion of the patient's spine. The device may also be used on the extremities, wherein the stabilizing member is positioned at the thorax and the force applying means is located at the end of the extremity to be examined, either the foot or the arm for imaging such soft tissue locations, for example, as the knee and elbow, respectively.

In another embodiment, the thorax engaging portion may comprise a vest or the like which is worn by the patient. A belt-like portion is provided to engage a portion of the patient's body remote from the thorax, such as the patient's hips when tractioning the spine, or the patient's buttocks, when compressing the spine. The vest and belt are joined by connectors such as rods, cables, or the like to produce the force necessary to compress or traction the spine.

Furthermore, a method for simulating a load on the patient's body during imaging procedures is also disclosed, and includes the steps of positioning a patient on a flat surface to subject the patient to an imaging procedure, engaging a thorax portion of the patient's body to stabilize the patient and prevent slippage on the flat surface, applying a force to a portion of the patient's body at a location remote from the thorax, and performing an imaging procedure on the patient while applying the force.

BRIEF DESCRIPTION OF THE DRAWINGS

The above features and other advantages of the present device and method will become more readily apparent as described below with respect to the detailed description of preferred embodiments, taken in conjunction with the following drawings, in which.

DETAILED DESCRIPTION OF THE PREFERRED EMBODIMENTS

Figure 1:
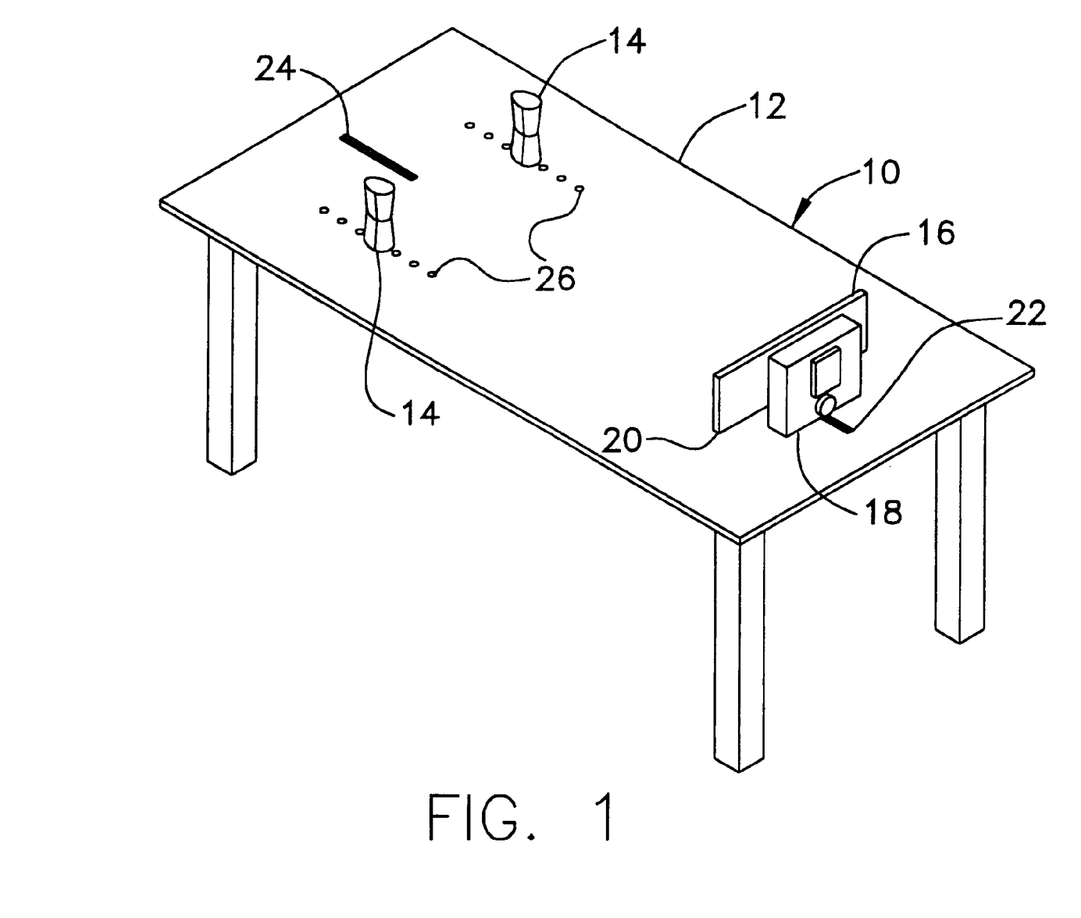
FIG. 1 illustrates a perspective view of a first embodiment of the present device.

Referring now to the drawings in which like reference numerals represent similar or identical elements throughout the several views, FIG. 1 illustrates the present device being utilized as part of an X-ray table or a table for a CAT scan or MRI machine. As illustrated in FIG. 1, in a first embodiment, the present device may comprise a table 10 which includes a flat portion 12 on which the patient may rest during the imaging procedure. Table 10 is provided with stabilizing posts 14 which are constructed of a material which will not affect the imaging procedure and are contoured to be positioned under the patient's axilla, or armpits, or against the shoulders of the patient, depending upon whether a portion of the patient's body will be compressed to simulate a weight load, or tractioned to remove all load from the body portion to be imaged. Table 10 also includes force generating device 16 having tensioning device 18 and body engaging bar 20, whose function will be described below. The positioning of the force generating device 16 and the stabilizing post 14 may be adjusted to compensate for the height of the person undergoing the imaging procedure, whereby post 14 may be moved, for example, by moving the posts in adjustment holes 26. The location of force generating device 16 may be varied by sliding device 16, for example, in adjustment slot 22.

The positioning of the posts 14 and the force generating device 16 as shown in FIG. 1 with respect to the flat surface 12 of the table 10 permits use of the compression/traction device to enhance the imaging of the thorax, lumbar or lower extremities of the person's body. The posts 14 would be positioned at the thorax portion, either against the shoulders or under the axilla of the patient's body, and the feet of the patient would be positioned against the body engaging bar 20 of the force generating device 16. Table 10 can be utilized to compress or traction the cervical portion of the patient's spine by moving the force generating device 16 from adjustment slot 22 to adjustment slot 24 so that the stabilizing posts 14 may still be positioned at the thorax portion of the patient's body while the body engaging bar 20 is positioned adjacent the patient's head, as will be described in detail below.

Figure 2:
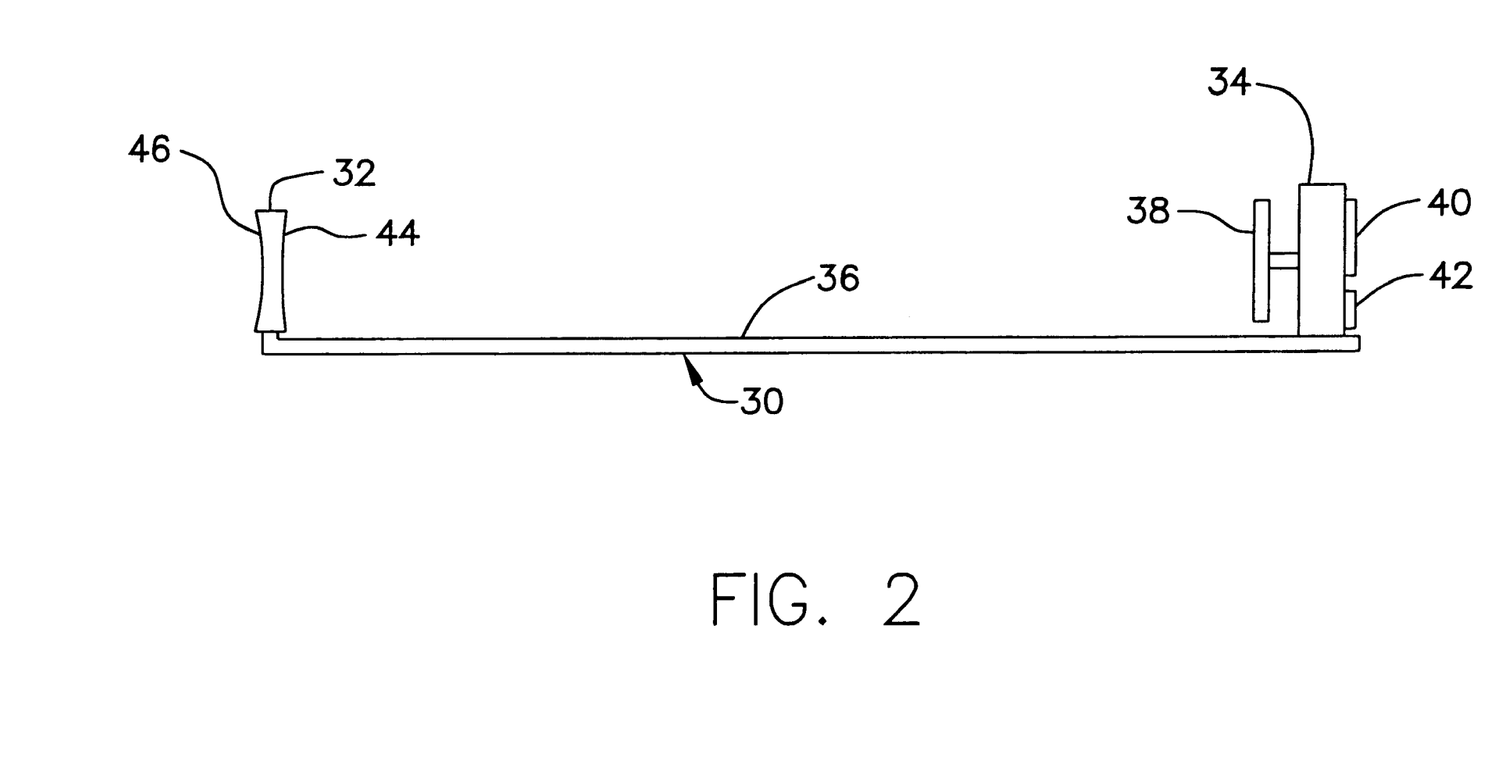
FIG. 2 illustrates a side elevation of a second embodiment of the device of FIG. 1.

A second embodiment of the compression/traction device is illustrated in FIG. 2. Compression/traction device 30 is portable and may be used to retrofit existing tables utilized with internal imaging devices. As seen in FIG. 2, compression/traction device 30 includes stabilizing members 32 (preferably two are provided, although only one is shown), and force generating device 34. Stabilizing members 32 and force generating device 34 are joined by an adjustable bridging member 36, which is adjustable to compensate for the height of the patient undergoing the imaging procedure and which is constructed of a material which will not affect the imaging procedure. Force generating device 34 includes body engaging bar 38 which is utilized to engage the feet or head of the patient depending upon the enhancement of the imaging procedure which is desired. Force generating device 34 also includes calibrated readout gauge 40, and force adjustment dial 42, which is utilized to vary the amount of force applied to body engaging bar 38, and the direction in which the force is applied. The force applied to body engaging bar 38 will be in a direction towards stabilizing members 32 for compression, and in a direction away from stabilizing members 32 for tractioning.

Force generating device 34 is preferably adjustable to vary the force applied to body engaging bar 38, and also adjustable to vary the direction of the force which is applied to the bar 38. The force generating device may be spring activated, or may include a gear box and motor to apply the force in the desired direction. Readout gauge 40 can indicate the amount of ft.-lbs. or other force measurement applied to the bar 38, and may comprise a gauge or dial which is analog or digital in its readout. The force generating device may also be microprocessor controlled or controlled by computer.

Figure 3:
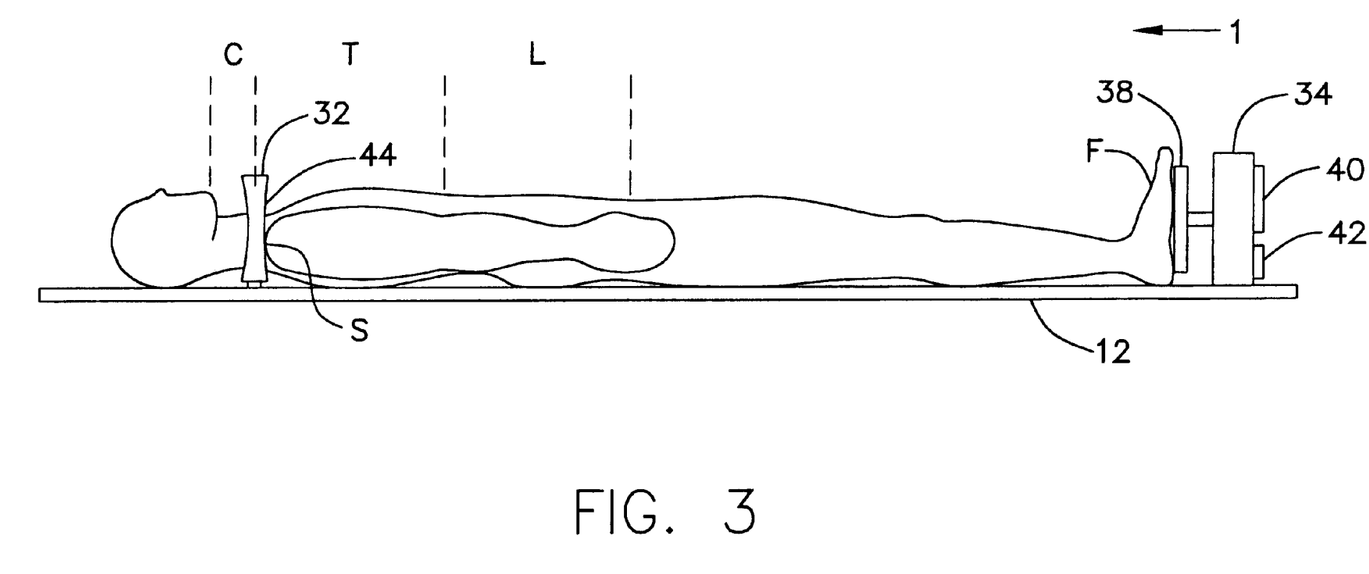
FIG. 3 illustrates a side elevation of a device of FIGS. 1 and 2 in use in which the patient's lumbar portion of the spine is being compressed to simulate a load.

FIGS. 3–6 illustrate the device for compression/traction during internal imaging procedures in use. In FIG. 3, the patient lays upon the flat surface 12 of the table and the compression/traction device 30 is adjusted so that the patient's feet F are placed against engaging bar 38. In order to simulate a load such as the weight of the person's body when imaging the lumbar portion L of the patient's spine, the stabilizing members 32 are placed against the shoulders S of the patient's body so that concave shoulder portion 44 rests against the shoulder S of the patient. Dial 42 is then activated to apply a force in the direction of arrow 1 to provide for compression to simulate the weight bearing load of the person's body on the lumbar portion L of the patient's spine. The amount of force applied is shown on readout gauge 40.

Figure 4:
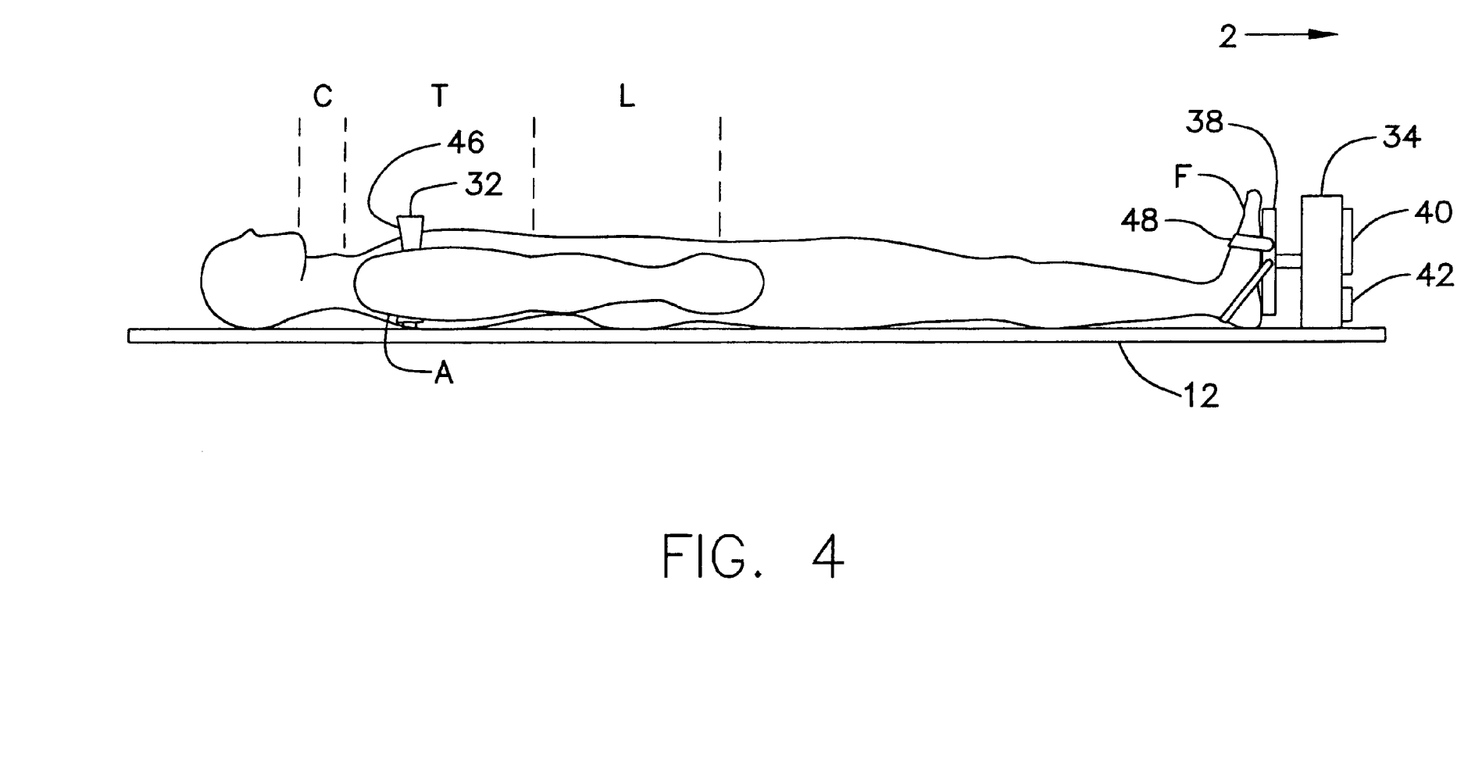
FIG. 4 illustrates a side elevation of a device of FIGS. 1 and 2 in use in which a lumbar portion of the patient's spine is being tractioned to remove any load on the lumbar portion of the spine.

FIG. 4 illustrates the compression/traction device being utilized to traction the lumbar portion of the patient's spine. In FIG. 4, the patient lays on the flat surface 12 of the table and the post members are positioned under the axilla A of the patient's thorax, i.e., the patient's armpits. Concave axilla pad 46 is positioned under the axilla, and the spacing between the stabilizing member and the force generating device 34 is adjusted so that the body engaging bar 38 is placed against the patient's feet F. A strap 48 is provided to engage the patient's feet F, and a force may be applied in the direction of arrow 2 to traction the patient's body by adjusting the dial 42. The force applied in the direction of arrow 2 is shown on readout gauge 40.

Figure 5:
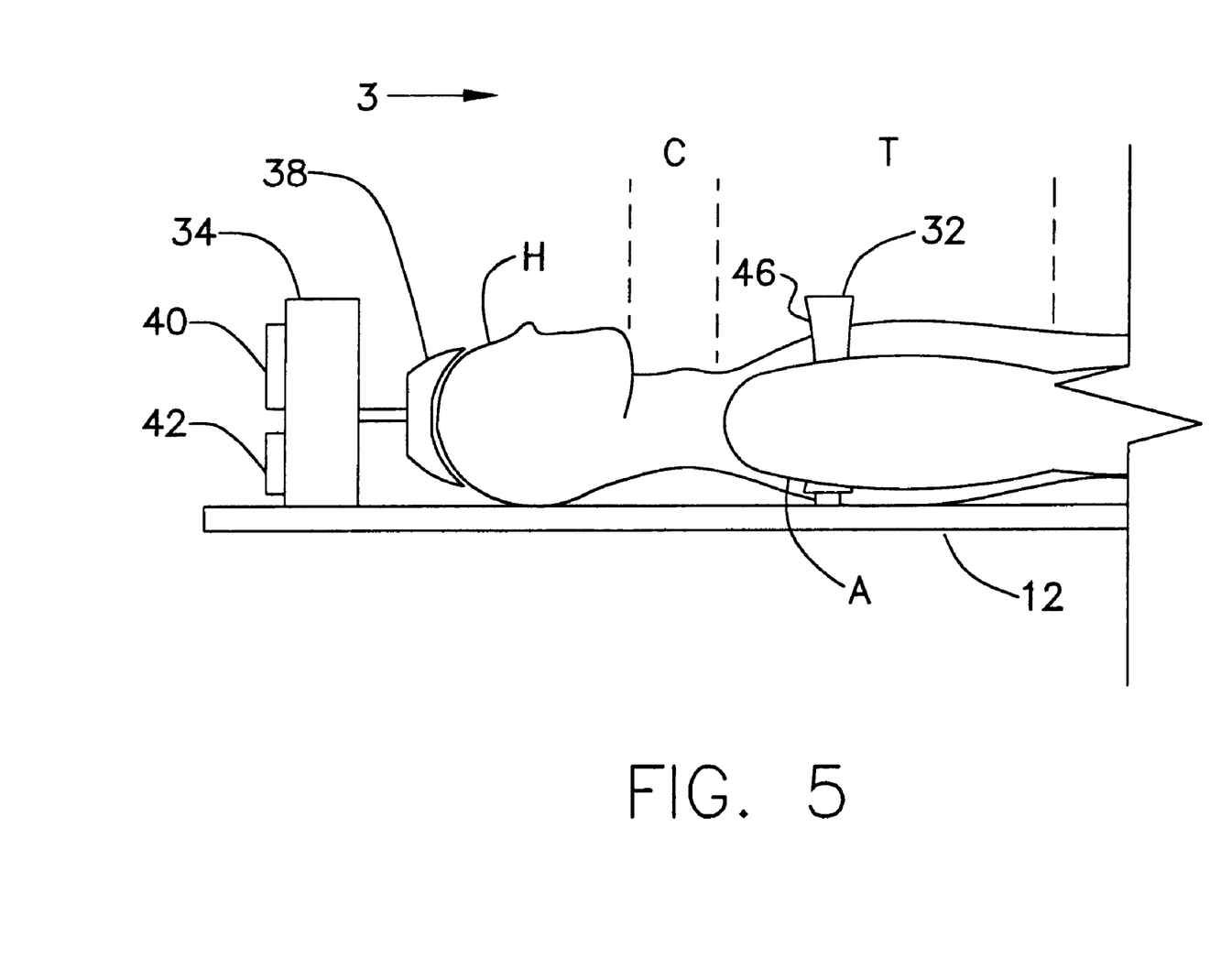
FIG. 5 illustrates a side elevation of a device of FIGS. 1 and 2 in which the cervical portion of the patient's spine is being compressed to simulate a load on the cervical portion of the spine.
Figure 6:
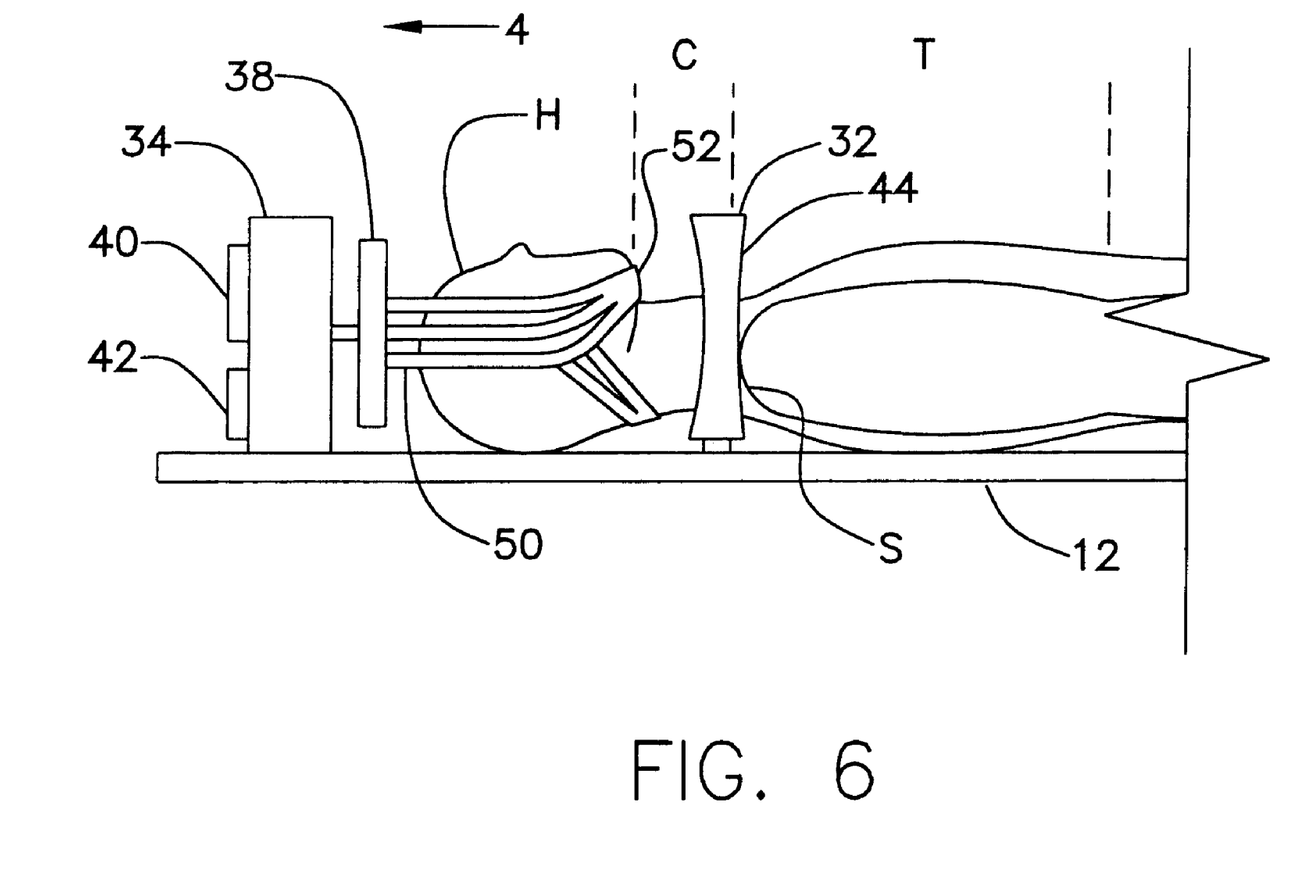
FIG. 6 illustrates a side elevation of a device of FIGS. 1 and 2 in which the cervical portion of the patient's spine is being tractioned to remove any load from the cervical portion of the spine.

FIGS. 5 and 6 illustrate the compression/traction device for providing compression or traction to a cervical portion of the patient's spine. In FIG. 5, stabilizing member 32 is positioned under the patient's axilla A so that concave axilla pad 46 engages the axilla A of the patient. Force generating device 34 is positioned adjacent the patient's head so that body engaging bar 38 engages the top of the patient's head H. Dial 42 is then adjusted to apply a force in the direction of arrow 3 to compress the cervical portion C of the patient's spine to simulate a load. The amount of force is shown on readout gauge 40.

FIG. 6 illustrates the device of FIG. 5 where the cervical portion C of the patient's spine is tractioned during the imaging procedure. In FIG. 6, body engaging bar 34 is provided with a head strap 50 which includes a chin and occiput pad 52 for engaging the chin and occiput of the patient. The stabilizing members 32 are positioned against the shoulders S of the patient so that concave shoulder pad 44 engages the shoulder S of the patient. Force generating device 34 is positioned adjacent the patient's head H so that body engaging bar 38 engages the top of the patient's head. Head strap 50 is positioned about the patient's head so that chin and occiput pad 52 engages the chin and occiput. Dial 42 is then adjusted to provide a force in the direction of arrow 4 to pull on the head to traction the cervical portion C of the patient's spine. The amount of force applied in the direction of arrow 4 is shown on readout gauge 40.

Figure 7:
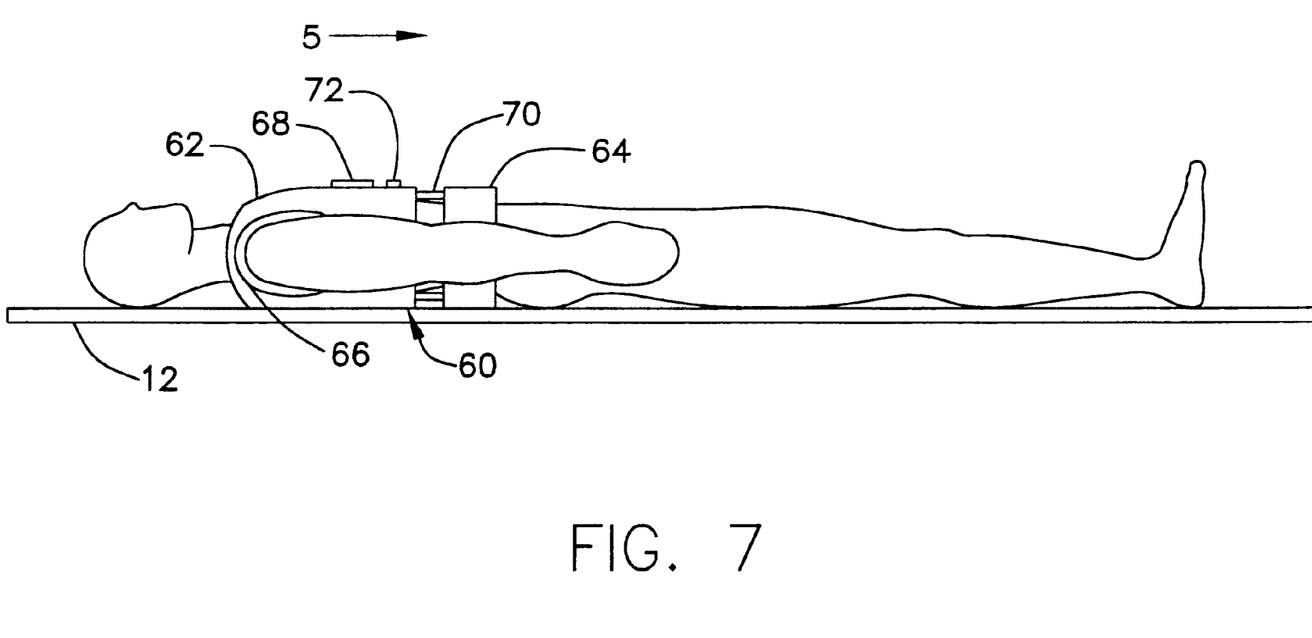
FIG. 7 illustrates a side elevation of a third embodiment of the present device in use in which the patient's spine is being tractioned to remove any load on the spine.
Figure 8:
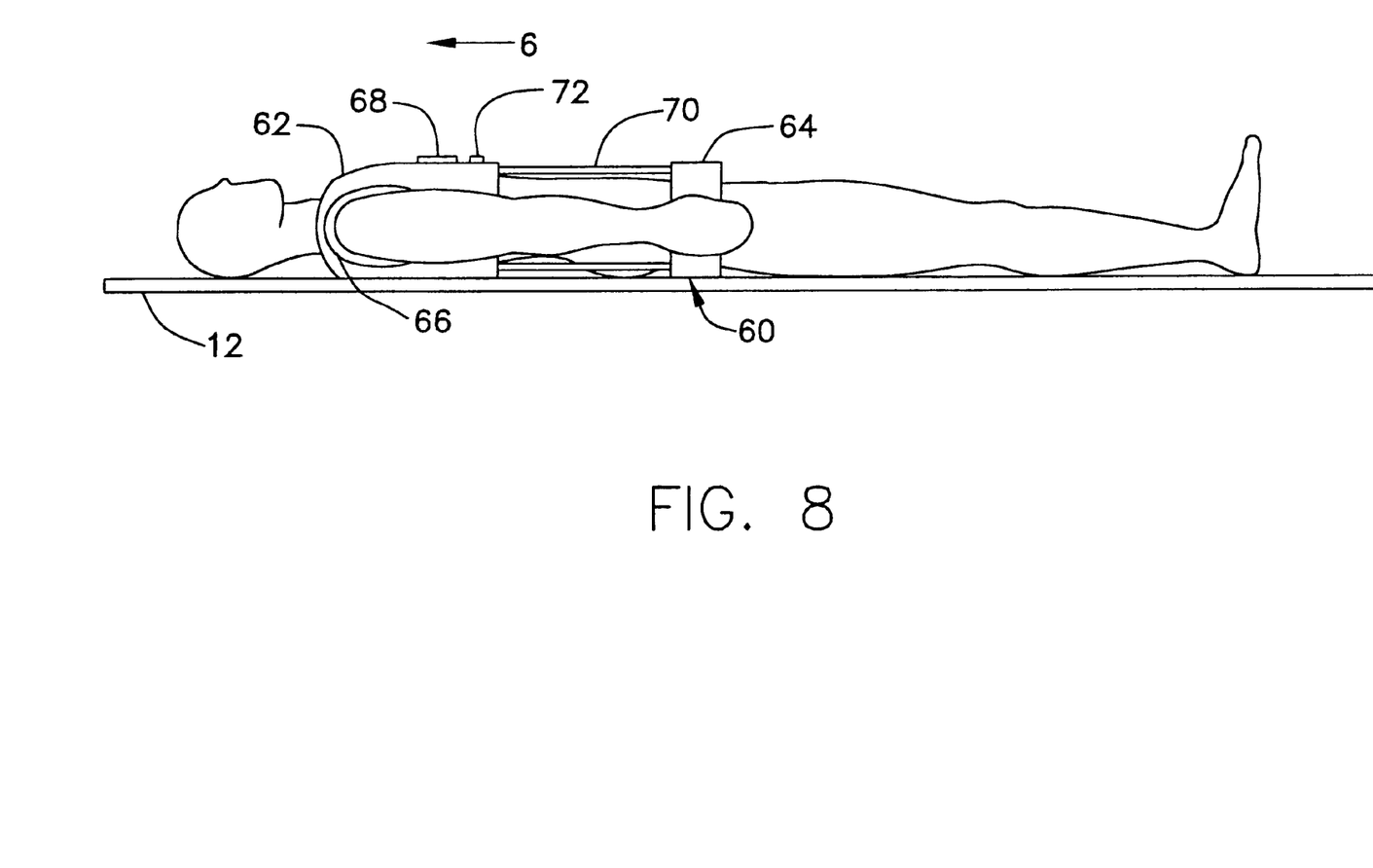
FIG. 8 illustrates a side elevation of the device of FIG. 7 in which the patient's spine is being compressed to simulate a load on the spine.

FIGS. 7 and 8 illustrate a further embodiment of the compression/traction device for providing compression or traction to the patient's spine. FIG. 7 illustrates the device 60 which is constructed with a vest-like portion 62 and a belt-like portion 64. There may be an opening (not shown) to enable the patient to don the vest and belt, and the opening may be held closed in a conventional manner, such as by snaps, hooks, zippers or the like. The device may also be two pieces to enable the technician or doctor to place the device on a patient who is in pain or who is unable to move. The two pieces will likewise be held closed in a conventional manner.

Vest 62 and belt 64 are joined by connectors 70, which may comprise rods, cables, belts, or the like. Preferably, there are two connectors on each side of the patient, although any number may be provided. For tractioning, belt 64 is moved towards vest 62 so that belt 64 is placed on the patient's hips and above his buttocks, as shown in FIG. 7. The vest 62 includes arm holes 66 so that the vest is worn to engage the thorax portion of the patient's body. Belt 64 engages a portion of the patient's body, the hips, remote from the thorax. After the vest and belt are donned by the patient or put on the patient by the technician or doctor, the patient lies on the flat portion 12 of the table. The belt is adjusted along connectors 70 to a comfortable position, and then adjustment knob 72 is manipulated to move belt 64 in the direction of arrow 5, away from vest 62, to traction or decompress the patient's spine. A gauge 68 may be provided to determine or record the amount of force applied to the spine. Knob 72 preferably controls the positioning of connectors 70 to move belt 64. Vest 62 is pushed against the patient's axilla at arm holes 66 during tractioning.

FIG. 8 illustrates device 60 in use during compression of the patient's spine to simulate a load on the spine. In this mode, belt 64 is manually adjusted so that it is positioned beneath the patient's buttocks as shown. After the patient dons the device 60, knob 72 is manipulated to move the belt 64 in the direction of arrow 6 to compress the spine. Vest 62 is pulled against the patient's shoulders during compression. Knob 72 controls positioning of the connectors 70 to move belt 64.

While the present invention has been described with respect to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A method for simulating a load on a patient's body during imaging procedures including X-ray, CAT scam, MRI and tomography procedures, comprising the steps of:

positioning a patient on a flat surface to subject the patient to an imaging procedure, engaging a thorax portion of the patient's body with a first stablizing member to stabilize the patient and prevent slippage on the flat surface, engaging at least one of the patient's head or feet with a second stabilizing member, wherein the second stabilizing member is connected to the first stabilizing member and movable to vary the distance between the first and second stabilizing members, applying a force to the patient's head or feet to compress the spine, measuring the force, and performing an imaging procedure on the patient while applying the force.

2. A method according to claim 1, wherein the engaging step includes holding the patient's body under the axilla of the thorax, and the applying step includes pulling on the legs or feet of the patient to traction a thorax and lumbar portion of the patient's body.

3. A method according to claim 1, wherein the step of engaging the thorax includes abutting the patient's shoulders, and the applying step includes pushing against the patient's feet to compress a thorax and lumbar portion of the patient's spine.

4. A method according to claim 1, wherein the step of engaging the thorax includes holding the patient's body under the axilla of the thorax, and the applying step includes pushing against the patient's head to compress a cervical portion of the patient's spine.

5. A method according to claim 1, wherein engaging step includes abutting the patient's shoulders, and the applying step includes pulling on the patient's head by engaging the patient's chin to traction a cervical portion of the patient's body.

* * * * *